United States Patent [19]
Jacobine et al.

[11] Patent Number: 5,837,751
[45] Date of Patent: Nov. 17, 1998

[54] NORBORNENYL AZLACTONES

[75] Inventors: Anthony F. Jacobine, Meridan; Steven T. Nakos, Andover, both of Conn.

[73] Assignee: Loctite Corporation, Hartford, Conn.

[21] Appl. No.: 619,068

[22] Filed: Nov. 28, 1990

[51] Int. Cl.$^6$ .......................... C08G 75/04; C08L 79/00; C08F 2/50
[52] U.S. Cl. .......................... 522/167; 522/146; 522/99; 522/180; 548/228
[58] Field of Search .............................. 522/99, 167, 180, 522/904, 146; 548/228

[56] References Cited

U.S. PATENT DOCUMENTS

| | | | |
|---|---|---|---|
| 4,339,589 | 7/1982 | Steglich et al. | 548/228 |
| 4,485,236 | 11/1984 | Rasmussen et al. | 544/69 |
| 4,619,867 | 10/1986 | Charbonneau et al. | 526/260 |
| 4,777,217 | 10/1988 | Rasmussen et al. | 525/283 |
| 4,777,276 | 10/1988 | Rasmussen et al. | 556/419 |
| 4,785,070 | 11/1988 | Rasmussen et al. | 528/73 |
| 4,808,638 | 2/1989 | Steinkraus et al. | 522/99 |
| 4,837,290 | 6/1989 | Rasmussen et al. | 526/304 |
| 4,981,972 | 1/1991 | Kobori et al. | 548/228 |
| 5,034,490 | 7/1991 | Jacobine et al. | 522/99 |
| 5,039,813 | 8/1991 | Fazio et al. | 548/228 |
| 5,081,197 | 1/1992 | Heilmann et al. | 526/260 |

FOREIGN PATENT DOCUMENTS

| | | |
|---|---|---|
| 419 283 | 3/1991 | European Pat. Off. . |
| 449 488 | 10/1991 | European Pat. Off. . |

OTHER PUBLICATIONS

Heilmann, et al., "Functional, Telechelic Polymers Derived From Reactions of Nucleophilic Oligomers and Alkenyl Azlactones, Part I: Telechelic Acrylamides Derived From Reactions of Alkenyl Azlactones and Amine–Terminated Oligomers," Advacnes In Polymer Synthesis, Culbertson, et al., ed., Plenum Press, pp. 203–233.

Product Data Sheet, "Vinyl Azlactone V.D.M.", SNPE Inc. (undated).

*Primary Examiner*—Susan W. Berman
*Attorney, Agent, or Firm*—Vidas, Arrett & Steinkraus, P.A.

[57] ABSTRACT

Norbornenyl functional azlactone compounds of the formula:

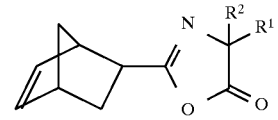

wherein $R^1$ and $R^2$ are independently monovalent hydrocarbon groups or $R^1$ and $R^2$, together with the carbon atom to which they are attached comprise a cyclic hydrocarbon group, are prepared by Diels-Alder addition of cyclopentadiene to vinyl azlactones. The norbornenyl azlactones are useful for preparing norbornenyl functional resins by azlactone ring opening reactions. The resulting resins may be employed as polyene components of curable thiol-ene formulations.

6 Claims, No Drawings

5,837,751

NORBORNENYL AZLACTONES

FIELD OF THE INVENTION

The invention pertains to novel norbornenyl azlactone compounds and to norbornenyl functional oligomers and polymers produced therefrom which are useful as polyene resins in curable thiol-ene compositions.

BACKGROUND OF THE INVENTION

U.S. Pat. No. 4,777,276 describes the preparation of certain (meth)acrylamido functional oligomers using specific alkenyl azlactones.

In U.S. Pat. No. 4,485,236 the alkenyl azlactones are reacted nucleophilically with secondary amino or mercapto functional compounds.

U.S. Pat. No. 4,777,217 discloses methacrylamido functional polymers produced by reaction of hydroxyfunctional polymers and isopropenyl azlactones.

U.S. Pat. No. 4,784,070 describes imidazdinone-containing polymers prepared by reaction of bisazlactones and diamines followed by cyclodehydration of the resulting polyamides.

U.S. Pat. No. 4,619,867 discloses use of alkenyl azlactones in a curable acrylic acid containing formula to produce a pressure sensitive adhesive.

Vinyl azlactone having the formula:

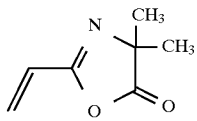

is commercially available from SNPE Inc., Princeton, N.J. Company literature on the product describes the known reactions of the compound.

Norbornenyl functional resins and their uses are described in U.S. Pat. No. 4,808,638 and references cited therein. The disclosed use of such resins in this reference is as the polyene resin in radically cured thiol-ene formulations.

The aforementioned U.S. patents are incorporated herein by reference.

SUMMARY OF THE INVENTION

In one aspect the invention comprises novel norbornenyl azlactone compounds having the formula:

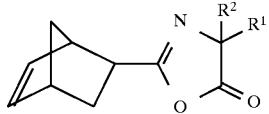

wherein $R^1$ and $R^2$ are independently monovalent hydrocarbon groups or $R^1$ and $R^2$, together with the carbon atom to which they are attached comprise a cyclic hydrocarbon group.

A second aspect of the invention comprises a process for producing the norbornenyl azlactones of the invention by Diels-Alder reaction of a vinyl azlactone with cyclopentadiene.

Still further aspects of the invention comprise the norbornene functional resins obtained from the inventive azlactones by ring opening addition reactions with primary amines or alcohols and the process for preparing such resins.

The norbornenyl functional resins produced from the novel azlactones are particularly suited for use as polyene resins in curable thiol-ene formulations of the type described in U.S. Pat. No. 4,808,638. Thus, a still further aspect of the invention is a curable thiol-ene composition in which the polyene component comprises a norbornenyl functional resin which is the ring opening addition reaction product of a norbornenyl azlactone of the invention with a compound having a plurality of nucleophilic groups.

DETAILED DESCRIPTION OF THE INVENTION

The norbornenyl azlactone compounds of the invention may be represented by the formula:

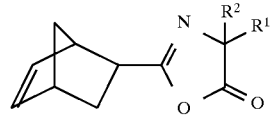

wherein $R^1$ and $R^2$ are independently monovalent hydrocarbon groups or $R^1$ and $R^2$, together with the carbon atom to which they are attached comprise a cyclic hydrocarbon group. Suitably $R^1$ and $R^2$ are selected from the group consisting of alkyl and cycloalkyl groups having 1 to 12 carbon atoms, and aryl and aralkyl groups having 6 to 12 carbon atoms or $R^1$ and $R^2$ taken together with the carbon atom to which they are attached form a 5 to 12 carbon atom cyclic hydrocarbon group. Conveniently, $R^1$ and $R^2$ are both methyl groups.

The inventive norbornenyl azlactone compounds may be prepared by Diels-Alder addition of cyclopentadiene to an vinyl azlactone compound of the formula:

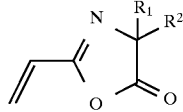

wherein $R^1$ and $R^2$ are as previously defined. The temperature utilized is one which is sufficient to allow Diels-Alder addition of the cyclopentadiene molecule to said vinyl azlactone. The reaction will proceed exothermically without catalyst at temperatures about room temperature or higher. Temperatures above about 30° C. are preferred. No substantial byproducts are produced by the reaction.

The starting vinyl azlactones are known from references described in the Background section above. Most preferably $R^1$ and $R^2$ are alkyl groups having 1 to 12 carbon atoms, conveniently methyl.

The norbornenyl azlactones of the invention will react with a wide variety of nucleophilic groups, particularly hydroxyl, primary or secondary amino and thiol groups, undergoing a ring opening addition. Preferably the nucleophile compound which is reacted with the norbornenyl azlactone of the invention includes a plurality of such groups. The resulting product has a plurality of groups of the formula:

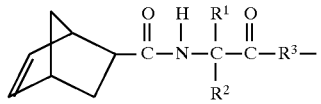

wherein $R^1$ and $R^2$ are independently monovalent hydrocarbon groups or $R^1$ and $R^2$, together with the carbon atom to which they are attached comprise a cyclic hydrocarbon group, $R^3$ is —$NR^4$—, —S—, or —O— and $R^4$ is H or alkyl. Preferably $R^3$ is —NH— or —O—.

Particularly suitable nucleophile compounds are organic or organosiloxane oligomers or high polymers having two or more hydroxyl or primary amino groups per molecule. Specific examples of nucleophile compounds are 1,6-hexanediol, 1,6-hexanediamine, 1,6-hexanedithiol, pentaerythritol, polyalkylene amines, amine terminated polyalkylene oxides, polyalkylene glycols such as polyethylene, polypropylene and polytetrabutylene glycols of various molecular weights, and alkylhydroxy, alkylthiol or alkylamino functional polydiorganosiloxanes.

A catalyst is required for hydroxyl and thiol nucleophiles are employed. Tertiary amines are preferred catalysts, although other known azlactone ring opening catalysts may also be employed. The more active tertiary amine catalysts, such as pyridine, 1,4-diazabicyclo[2.2.2]octane (DABCO), 4-dimethylaminopyridine (DMAP), 1,5-diazabicyclo[4.3.0]non-5-ene (DBN), and 1,8-diazabicyclo-[5.4.0]undec-7-ene (DBU) are preferred. When the nucleophile group is a primary amine, no catalyst is necessary. Secondary amines may or may not require a catalyst, depending on the particular amine employed.

Further examples of azlactone ring opening catalysts, suitable nucleophiles and reaction conditions may be found, for example in U.S. Pat. Nos. 4,777,276 and 4,777,217.

Unlike ring opening reactions of vinyl azlactones for which Michael addition to the vinyl group can be a substantial side reaction, the norbornenyl azlactones of the invention do not undergo a competitive reaction at the norbornene double bond during the ring opening step. Consequently the reaction is generally easier to control and produces a cleaner product than ring opening reactions on the starting vinyl azlactone.

The ring opening reaction products having a plurality of norbornenyl groups of the formula:

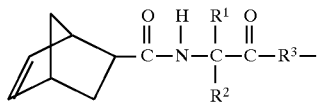

wherein $R^1$ and $R^2$ are independently monovalent hydrocarbon groups or $R^1$ and $R^2$, together with the carbon atom to which they are attached comprise a cyclic hydrocarbon group, $R^3$ is —$NR^4$—, —S—, or —O— and $R^4$ is H or alkyl, are especially suitable for use as the polyene component in curable thiol-ene compositions. Such compositions comprise a polyene, a polythiol and an initiator of thiol-ene addition reactions, typically a free radical initiator. Generally the total functionality of the system (obtained by adding the average number of thiol groups per polythiol molecule to the average number of ene groups per polyene) will be greater than 4 so that the composition cures to a crosslinked solid. Suitably the thiol-ene formulations have a ratio of thiol groups to ene groups of between about 0.7:1 and 1:1.3, preferably about 1:1.

The invention may be illustrated by the following non-limiting examples.

EXAMPLE 1

Freshly distilled cyclopentadiene (262.3 g, 3.97 moles) was added dropwise at 40° C. to 501.66 g (3.61 moles) vinyl azlactone V.D.M., a compound sold by SNPE Inc., having the formula:

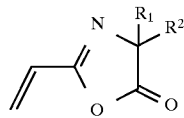

During the addition, the temperature rose to 90°–100° C. This temperature range was maintained for two hours after the addition, at which time excess cyclopentadiene was removed by rotary evaporation. The crude product was then subjected to vacuum distillation, removing a small forecut at 50° C., 2 mm Hg pressure, followed by the product at 70°–73° C., 0.2 mm Hg. Yield: 689.7 g (93%) of a colorless liquid that rapidly solidified upon standing at room temperature.

The product, designated NAZ, was a compound of the formula:

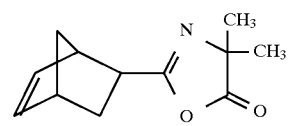

EXAMPLE 2

Preparation and Cure of Polyol/Norbornenyl Azlactone Adduct

A poly(tetramethylene ether) polyol with hydroxyl termination possessing 3.087 meq. total OH/g reactive functionality (Polymeg 650, 200.0 g, 0.617 eq. OH) was added to 130.36 g (0.636 mole) NAZ and 3.31 g DBU. The reaction contents were stirred and heated to 100° C. Reaction progress was followed by IR spectroscopy. The azlactone C=O stretch at 1817 cm$^{-1}$ rapidly diminished after 2 hours and was barely detectable after 8 hours. Simultaneously, the linear ester C=O stretch of 1739 cm$^{-1}$ began to form and reached a maximum in the same time period. At this time, the reaction mixture was transferred to a 2 inch diameter wiped film evaporator and vacuum stripped at a rate of ~200 ml/hr at 125° C., 0.4 mm Hg, giving the product (Adduct A) as a viscous, amber syrup, weighing 314.8 g (96%).

A curable thiol-ene composition was prepared as follows:

30 grams Adduct (A)

6.91 grams pentaerythritoltetrakis (3-mercaptopropionate)

2% Darocur® 1173 photoinitiator 1000 ppm Wako® Q1301 stabilizer

A 10 mil (0.25 mm) film was cured by UV irradiation (310 mJ/cm$^2$ per side) from a medium pressure Hg lamp. A transparent, dry-to-the-touch film resulted.

EXAMPLE 3

Preparation and Cure of Polyetheramine/ Norbornenyl Azlactone Adduct

A poly(propylene ether) with amine termination possessing 0.96 meq. $NH_2$/g (Jeffamine® 2000, 200.0 g, 0.192 eq $NH_2$) was added to 40.54 g (0.198 mole) NAZ. The reaction contents were stirred and heated to 100° C. for 8 hours. Reaction progress was followed by IR spectroscopy. The azlactone C=O stretch at 1817 cm$^{-1}$ was no longer detectable after 8 hours. At this time, the reaction mixture was vacuum stripped on a rotary evaporator for 2 hours at 75° C., 0.2 mm Hg, giving the product (Adduct B) as a yellow syrup, weighing 239.3 g (99%).

A thiol-ene cured film was prepared as follows:
30 grams Adduct (B)
3.00 grams pentaerythritoltetrakis(3-mercaptopropionate)
2% Darocur® 1173
1000 ppm Wako® Q1301

A 10 mil (0.25 mm) film was cured by UV irradiation (310 mJ/cm$^2$ per side) from a medium pressure Hg lamp. A transparent, dry-to-the-touch film resulted.

EXAMPLE 4

Preparation of Polyetheramine/Norbornenylazlactone Adduct

A 500 MW polyoxypropylenetriamine, possessing 5.81 meq $NH_2$/g (Jeffamine T-403, 25.0 g, 0.145 eq $NH_2$) was added to 29.78 g (0.145 mole) NAZ and 40 ml toluene. The reaction contents were stirred and heated to 100° C. Reaction progress was followed by IR spectroscopy. The azlactone C=O stretch at 1817 cm$^{-1}$ was no longer detectable after 14 hours. At this time, the reaction mixture was vacuum stripped on a rotary evaporator for 1 hour at 75° C. at 20 mm Hg, giving the product (Adduct C) as a thick, yellow syrup.

EXAMPLE 5

Preparation of Polyetheramine/Norbomenylazlactone Adduct

A 3000 MW polyoxypropylene triamine with amine termination, possessing 0.92 meq $NH_2$/g (Jeffamine T-3000, 50.0 g, 0.046 eq $NH_2$) was added to 9.43 g (0.046 mole) NAZ and 60 ml toluene. The reaction contents were stirred and heated to 100° C. Reaction progress was followed by IR spectroscopy. The azlactone C=O stretch at 1817 cm$^{-1}$ was no longer detectable after 6 hours. At this time, the reaction mixture was vacuum stripped on a rotary evaporator for 1.5 hours at 77° C. at 20 mm Hg, giving the product (Adduct D) as a yellow syrup.

EXAMPLE 6

Preparation of Polyethereamine/Norbomenylazlactone Adduct

A 5000 MW polyoxypropylene triamine with amine termination, possessing 0.55 meq $NH_2$/g (Jeffamine T-5000, 55.0 g, 0.028 eq $NH_2$) was added to 5.68 g (0.028 mole) NAZ and 60 ml toluene. The reaction contents were stirred and heated to 100° C. Reaction progress was followed by IR spectroscopy. The azlactone C=O stretch at 1817 cm$^{-1}$ was no longer detectable after 8 hours. At this time, the reaction mixture was vacuum stripped on a rotary evaporator for 2 hours at 77° C. at 20 mm Hg, giving the product (Adduct E) as a yellow syrup.

EXAMPLE 7

Preparation and Cure of 3-Aminopropyl Terminated Polydimethylsiloxane/Norbomenylazlactone Adduct A polydimethylsiloxane with aminopropyl termination, possessing 0.5 meq $NH_2$/g (Genesee Polymers GP-174, 125.0 g, 0.062 eq $NH_2$) was added to 12.43 g (0.061 mole) NAZ and 60 ml toluene. The reaction contents were stirred and heated to 100° C. Reaction progress was followed by IR spectroscopy. The azlactone C=O stretch at 1817 cm$^1$ was no longer detectable after 12 hours. At this time, the reaction mixture was stripped on a rotary evaporator for 2 hours at 77° C. at 0.2 mm Hg, giving the product (Adduct F) as a yellow syrup.

Cured films of Adduct F were prepared as follows:
60 grams Adduct F, 0.027 eq norbornene
17.9 grams 3K5M (3000 MW dimethylsiloxy/mercaptopropylmethylsiloxane copolymer containing 1.52 meq thiol/g), 0.027 eq thiol
2 wt % Darocur® 1173
500 ppm Wako® Q1301

UV cure at 1785 mJ/cm$^2$ medium pressure Hg per side into a 10 mil film. A transparent, dry-to-the-touch film resulted.

What is claimed is:

1. A curable thiol-ene composition comprising a polyene, a polythiol and an initiator of thiol-ene addition reactions wherein the polyene component comprises a compound having a plurality of groups of the formula:

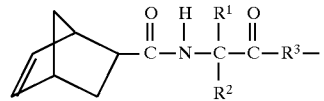

wherein $R^1$ and $R^2$ are independently monovalent hydrocarbon groups or $R^1$ and $R^2$, together with the carbon atom to which they are attached comprise a cyclic hydrocarbon group $R^3$ is —$NR^4$—, —S—, or —O— and $R^4$ is H or alkyl.

2. A curable thiol-ene composition as in claim 1 wherein $R^1$ and $R^2$ are selected from the group consisting of alkyl and cycloalkyl groups having 1 to 12 carbon atoms, and aryl and aralkyl groups having 6 to 12 carbon atoms or $R^1$ and $R^2$ taken together with the carbon atom to which they are attached form a 5 to 12 carbon atom cyclic hydrocarbon group.

3. A curable thiol-ene composition as in claim 2 wherein $R^1$ and $R^2$ are both methyl groups.

4. A curable thiol-ene composition as in claim 3 wherein $R^3$ is —NH— or —O—.

5. A curable thiol-ene composition as in claim 1 wherein the ratio of thiol to ene groups in the composition is between 0.7:1 and 1:1.3.

6. A curable thiol-ene composition as in claim 1 wherein the total functionality of the composition is greater than 4.

* * * * *